(12) United States Patent
Lovell (10) Patent No.: US 9,308,357 B2
(45) Date of Patent: Apr. 12, 2016

(54) CYST EXTRACTOR

(71) Applicant: Gary Lovell, Rexburg, ID (US)

(72) Inventor: Gary Lovell, Rexburg, ID (US)

( * ) Notice: Subject to any disclaimer, the term of this patent is extended or adjusted under 35 U.S.C. 154(b) by 266 days.

(21) Appl. No.: 14/055,754

(22) Filed: Oct. 16, 2013

(65) Prior Publication Data

US 2015/0105755 A1    Apr. 16, 2015

(51) Int. Cl.
*A61B 17/00* (2006.01)
*A61B 17/3205* (2006.01)
*A61M 25/00* (2006.01)
*A61M 27/00* (2006.01)
*A61B 17/34* (2006.01)
(Continued)

(52) U.S. Cl.
CPC ............ *A61M 27/00* (2013.01); *A61B 17/3205* (2013.01); *A61B 17/3421* (2013.01); *A61B 2017/00287* (2013.01); *A61B 2017/00349* (2013.01); *A61B 2017/00358* (2013.01); *A61B 2017/00818* (2013.01); *A61B 2017/00823* (2013.01); *A61B 2017/00902* (2013.01); *A61B 2017/22079* (2013.01); *A61B 2017/3419* (2013.01); *A61B 2017/3445* (2013.01); *A61B 2017/3458* (2013.01); *A61B 2017/3466* (2013.01); *A61B 2017/3488* (2013.01); *A61B 2019/5219* (2013.01); *A61B 2217/005* (2013.01); *A61B 2218/007* (2013.01); *A61M 2202/0014* (2013.01)

(58) Field of Classification Search
CPC ........... A61B 17/3205; A61B 17/3421; A61B 2017/00287; A61B 2017/00349; A61B 2017/00818; A61B 2017/00823; A61B 2017/00902; A61B 2017/3419; A61B 2017/3445; A61B 2017/3458; A61B 2017/3466; A61B 2017/3488; A61B 2019/5219; A61B 2217/005; A61B 2218/007; A61B 2017/00358; A61B 2017/22079; A61B 17/12; A61B 2017/12004; A61B 17/12009; A61B 17/12013; A61B 2017/12018; A61M 2202/0014; A61M 27/00; A61M 1/0039; A61M 1/0041; A61M 1/008

See application file for complete search history.

(56) References Cited

U.S. PATENT DOCUMENTS

| 958,854 | A | * | 5/1910 | Bunn | ............................. 27/24.2 |
| 2,911,968 | A | * | 11/1959 | Schueler | .............. A61B 1/2676 600/187 |
| 3,592,199 | A | * | 7/1971 | Ostensen | ............... A61B 1/267 362/197 |

(Continued)

FOREIGN PATENT DOCUMENTS

| CN | 2549916 Y | 7/2002 |
| CN | 201171684 Y | 9/2007 |

(Continued)

*Primary Examiner* — Adam Marcetich
(74) *Attorney, Agent, or Firm* — Schmeiser, Olsen & Watts LLP (57) ABSTRACT

A cyst extractor allows a medical practitioner to retract, aspirate, ligate and amputate a cyst or cystic mass within a patient under regional anaesthesia and minimally invasive incision. A cyst extractor may include a transparent tubular member with a cap coupled to one end. The cap may have at least one view port that has a magnifying lens. The cap may also have a needle port through which a needle is inserted to puncture the cyst. A trap may be in fluid communication with the transparent tubular member. A suction post is in communication with the trap in order to pull the contents of an aspirated cyst into the trap. A light post containing a light source may be connected to the transparent tubular member in order to illuminate the interior of the extractor. A ligature deployer and a cutting wire may also be coupled to the tubular member.

14 Claims, 9 Drawing Sheets

(51) Int. Cl.
*A61B 17/22* (2006.01)
*A61B 19/00* (2006.01)

(56) References Cited

U.S. PATENT DOCUMENTS

| | | | | |
|---|---|---|---|---|
| 3,685,509 | A * | 8/1972 | Bentall | A61B 1/303 600/583 |
| 4,700,694 | A | 10/1987 | Shishido | |
| 4,958,621 | A | 9/1990 | Topel et al. | |
| 5,169,397 | A * | 12/1992 | Sakashita | A61B 1/00071 600/105 |
| 5,234,426 | A | 8/1993 | Rank et al. | |
| 5,261,905 | A | 11/1993 | Doresey, III | |
| 5,314,406 | A * | 5/1994 | Arias | A61B 17/3203 604/167.04 |
| 5,320,630 | A | 6/1994 | Ahmed | |
| 5,531,722 | A * | 7/1996 | Van Hale | A61C 1/052 433/116 |
| 5,573,496 | A | 11/1996 | McPherson et al. | |
| 5,810,806 | A * | 9/1998 | Ritchart | A61B 10/0266 604/21 |
| 6,027,502 | A * | 2/2000 | Desai | A61B 18/1482 604/131 |
| 6,280,415 | B1 * | 8/2001 | Johnson | A61B 17/0218 433/91 |
| 6,558,379 | B1 * | 5/2003 | Batchelor | A61B 18/1482 604/21 |
| 2002/0026199 | A1 * | 2/2002 | Fortier | A61B 17/00234 606/108 |
| 2004/0143169 | A1 * | 7/2004 | Branch | A61B 19/52 600/245 |
| 2004/0158261 | A1 | 8/2004 | Vu | |
| 2005/0143757 | A1 * | 6/2005 | Ghareeb | A61B 17/12013 606/139 |
| 2005/0251162 | A1 * | 11/2005 | Rothe | A61B 17/0401 606/153 |
| 2007/0225734 | A1 | 9/2007 | Bell et al. | |
| 2008/0091061 | A1 * | 4/2008 | Kumar | A61B 1/00068 600/104 |
| 2008/0091074 | A1 * | 4/2008 | Kumar | A61B 1/00071 600/156 |
| 2011/0046442 | A1 * | 2/2011 | Matsushita | A61B 1/00071 600/114 |
| 2011/0152776 | A1 * | 6/2011 | Hartoumbekis | A61B 1/126 604/167.01 |
| 2012/0035532 | A1 | 2/2012 | Melsheimer et al. | |
| 2012/0035622 | A1 | 2/2012 | Kiser et al. | |
| 2013/0046316 | A1 | 2/2013 | Sullivan et al. | |

FOREIGN PATENT DOCUMENTS

| | | |
|---|---|---|
| CN | 201384532 Y | 12/2008 |
| CN | 202078632 U | 5/2011 |
| EP | WO2004002334 | 1/2004 |
| RO | 120809 B1 | 1/2004 |

* cited by examiner

CYST EXTRACTOR

BACKGROUND OF THE INVENTION

1. Technical Field

This invention relates to a medical device and method for removing fluid or semi-fluid lesions from the body such as a cystic mass, infected appendix, gallbladder or the like.

2. Background Art

Medical Practitioners are often required to remove or repair fluid or semi-fluid filled masses or organs in the abdomen that are of an inherent infectious or inflammatory nature should they rupture and spill into the abdomen. For example, gynecologists are often required to remove malignant, sebaceous or endometriotic ovarian cysts whose fluids are best contained and isolated from healthy tissues. Similarly, physicians are also often required to remove infected ovaries, fallopian tubes, appendixes or gallbladders whose contents are best contained and isolated.

These surgical procedures are commonly done laparoscopically which involves remote access with multiple punctures of the abdominal wall which incisions have inherently greater risks for the patient of both a medical cost, and safety nature. Laparoscopic approaches to large masses are often associated with spillage and contamination of the peritoneal cavity. Retrieval of these tissues requires extending incisions, and often is associated with fragmentation of the specimen and spillage. If fluid from a malignant ovarian cyst spills, it advances the stage of the cancer and may increase the aggressiveness of the treatment required to treat the cancer. Additionally, laparoscopy requires general anaesthesia, as opposed to regional or spinal anaesthesia which is inherently safer, and affords a more pain free recovery period.

Several different medical devices have been developed in order to aid in these types of surgeries. For example, Chinese Patent CN2549916Y issued to Applicant SHI XUEFANG illustrates a tube through which a needle passes to puncture a fluid filled mass. Suction is applied to the tube in order to aspirate the fluid from the mass. This suction, however, is applied by use of a suction bulb. It is also difficult for the medical practitioner to determine exactly what is occurring inside the tube as it has multiple layers which are not transparent.

Other medical devices such as that disclosed in US Publication No. US 2004/0158261 are very complicated and many things could go wrong during their operation. US 2004/0158261 discloses a device for removing an ovarian cyst that utilizes a sack that encapsulates the cyst and then removes it. This, however, requires that the cyst fit in the sack and that the medical practitioner utilizing the device can encircle the cyst without complications. These limitations reduce the viability of the medical device disclosed in this publication.

Accordingly, what is needed is a medical device for draining and removing cystic masses, appendixes, gallbladders and the like, which is relatively uncomplicated and allows the medical practitioner to easily view, manipulate, aspirate, and amputate the contents and the lesion being removed or repaired through a small incision without the requirement of inflation of the abdomen or a pneumoperitoneum and general anaesthesia.

DISCLOSURE OF THE INVENTION

The cyst extractor, as disclosed hereafter in this application, may be used to operate on and remove diseased cystic masses, cystic lesions, lesions, ovarian tumors, abscesses, appendixes, gallbladders and the like.

In particular embodiments, a cyst extractor may include a tubular member, wherein the tubular member is translucent. A cap coupled to an end of the tubular member, further comprises at least one view port and at least one needle port. A trap may be in fluid communication with the tubular member. The trap would also be in communication with a suction post. A light post may also be coupled to the tubular member.

Additional embodiments of a cyst extractor may include a transparent tubular member with a cap coupled to one end of the transparent tubular member. The cap further has at least one view port. A trap may be in fluid communication with the transparent tubular member. The trap may also be in communication with a suction post. A light post may be connected to the transparent tubular member. A ligature deployer and a cutting wire may also be attached to the transparent tubular member.

A method for removing a cystic lesion from a patient using a cyst extractor may begin with making an incision in the patient. Next the medical practitioner may insert a cyst extractor into the incision wherein an end of the cyst extractor is placed adjacent the cystic lesion. Suction is then applied to the cyst extractor. The cystic lesion is retracted into the cyst extractor and then the cystic lesion is removed from the patient's body.

The foregoing and other features and advantages of the cyst extractor will be apparent to those of ordinary skill in the art from the following more particular description of the invention and the accompanying drawings.

BRIEF DESCRIPTION OF THE DRAWINGS

The invention will hereinafter be described in conjunction with the appended drawings where like designations denote like elements, and.

DESCRIPTION OF THE INVENTION

As discussed above, a medical device for removing a cystic lesion such as an ovarian cyst from a patient may include a tubular member, a trap, a suction post, a light post, a lens and a needle. For the purposes of this application, a cystic lesion, lesion, cystic body or cyst may include any liquid, or semi-solid filled organ, sack, cyst or the like which is surrounded by a layer of tissue and contained within a patient's body. Examples of cystic lesions, lesions, cystic bodies or cysts as per this definition include pelvic cysts and abscesses of the ovary, tube, appendix, and similarly those of the gallbladder.

FIGS. 1-6 illustrate an embodiment of a cyst extractor 10. A cyst extractor 10 configured according to this embodiment includes a cannula or tubular member 12. The tubular member 12 may comprise a hollow cylindrical tube approximately 30 to 50 centimeters in length and with an approximately 1½ to 4 centimeter diameter. The tubular member 12 may also be translucent, transparent or the like, in order to allow light to travel throughout the cyst extractor 10. The transparency of the tubular member 12 also allows the medical practitioner to see what is happening inside the cyst extractor 10. The tubular member 12 should also be formed from a material which is inexpensive, in order to allow the cyst extractor 10 to be disposable.

The tubular member 12 may be formed in any shape desired. It may also have any cross section desired, i.e. rectangular, square, circular, triangular, oval, octagonal and the like. The tubular member 12 may also be formed from any material desired so long as it is transparent, strong enough to withstand suction, inexpensive and medical grade. The tubular member 12 may also be any diameter and length desired.

One end of the tubular member 12 is coupled to a cap 14. The cap 14 seals the end of the tubular member 12. The cap 14 may be any size or shape that matches, is slightly smaller or slightly larger than the size and shape of the cross section of the tubular member 12. The cap 14 may be removably coupled to the tubular member 12 or the cap 14 may be formed as an integral part of the tubular member 12. It may be desirable that the coupling between the cap 14 and the tubular member 12 is air tight.

The cap 14 has a view port 24 formed in it. The view port 24 is an opening in the cap 14, through which the medical practitioner can view the cyst and the procedure as it is performed. The view port 24 may be lens-like for magnification, and round as illustrated in the images, or it may be square, oval, rectangular, triangular or the like. The view port 24 may also be any size desired, so long as it does not fill the entire cap 14 or is too small to see through.

The view port 24 may contain a lens 25. The lens 25 may be simply a transparent cover for the view port 24 or the lens 25 may be a magnifying lens. The lens 25, if a magnifying lens, may magnify to any degree desired in order to better allow the medical practitioner to view the procedure taking place at the other end of the cyst extractor 10.

In alternate embodiments, there may be multiple view ports 24 with multiple lenses 25 all of differing magnification.

In additional embodiments, multiple lenses 25 may be hinged so that the medical practitioner of the cyst extractor 10 is able to choose the magnification that they use.

Also formed in the cap 14 is a needle port 26. The needle port 26 is an opening formed in the cap 14. The needle port 26 may be any size or shape desired.

Figure 1:
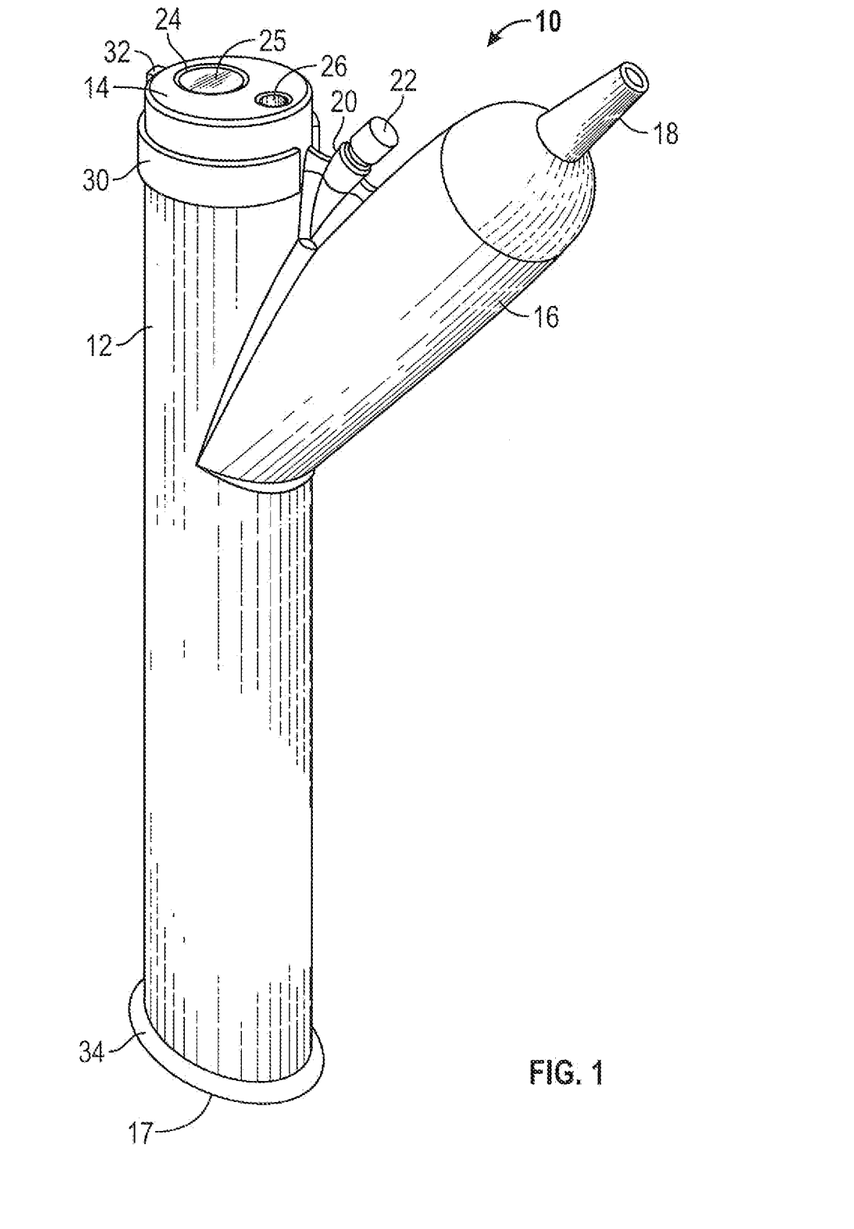
FIG. 1 is an isometric view of a cyst extractor.
Figure 2:
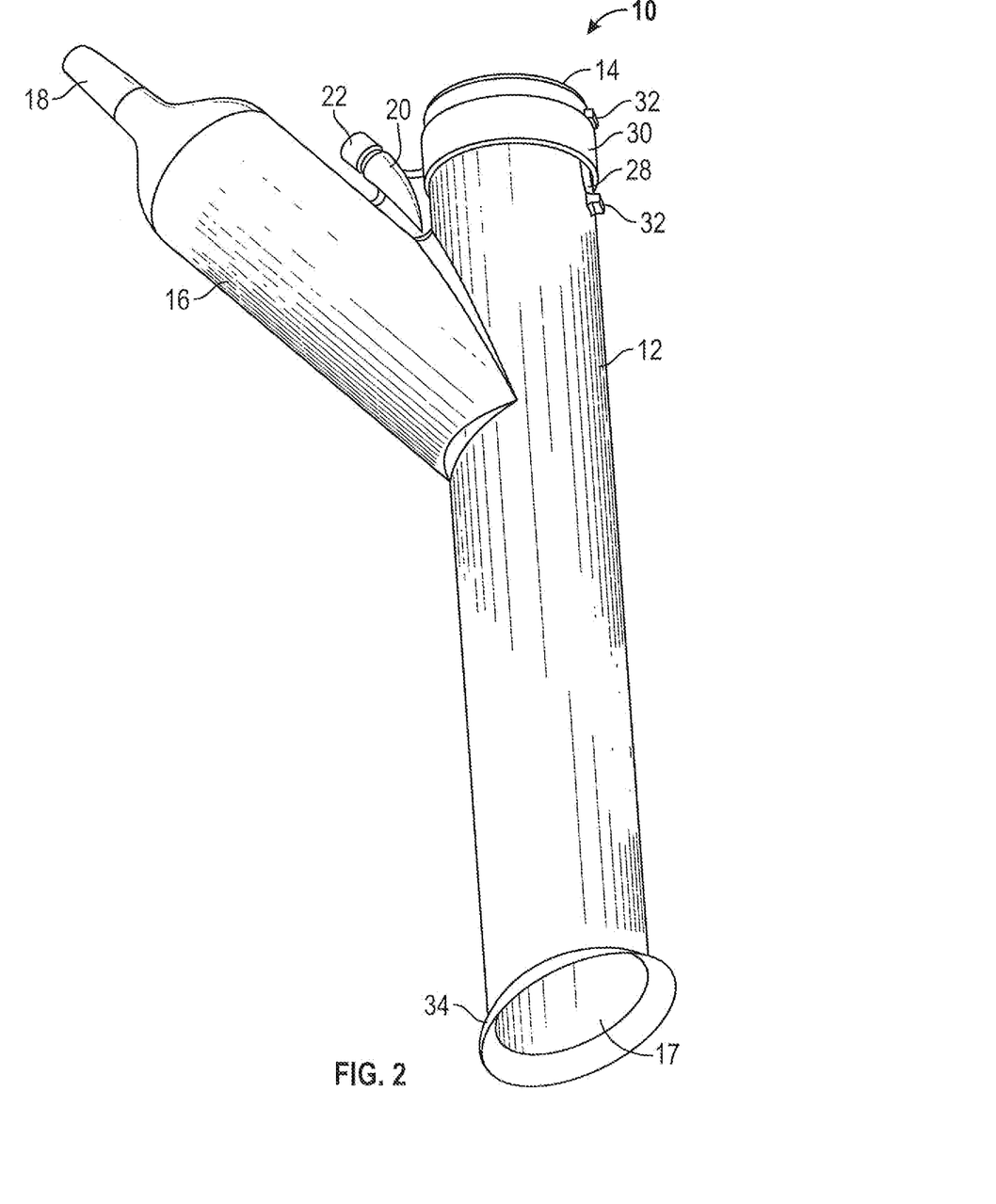
FIG. 2 is a rear isometric view of a cyst extractor.
Figure 3:
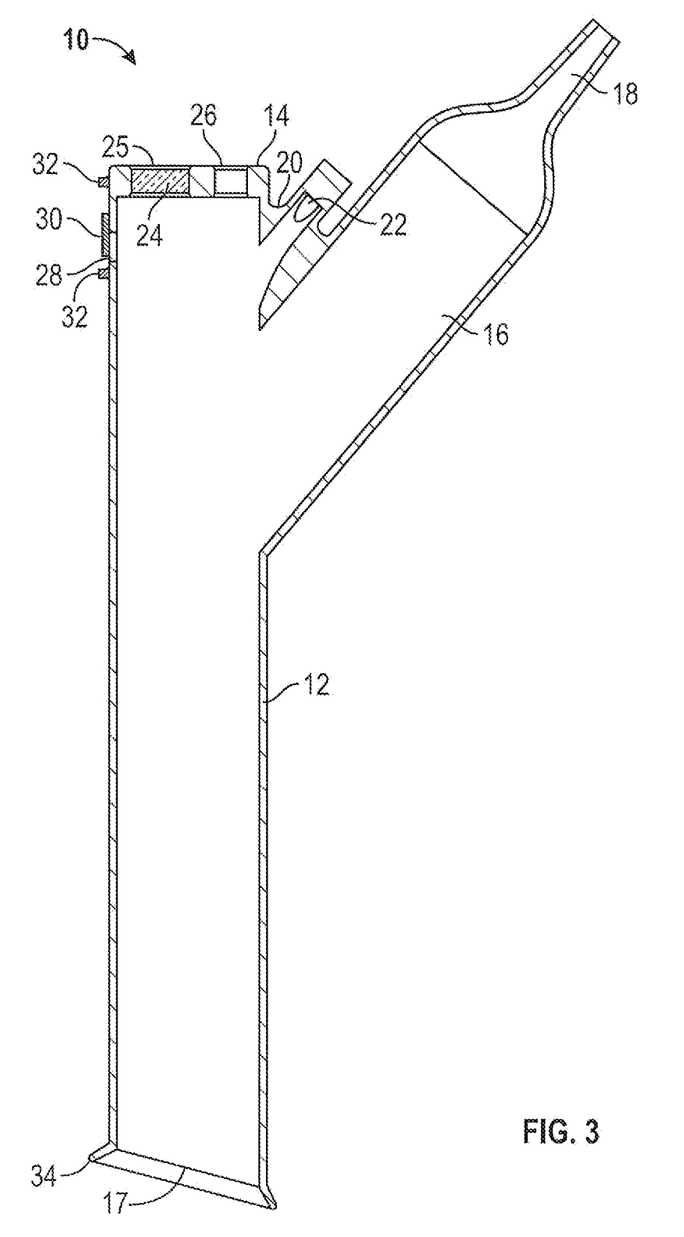
FIG. 3 is a cross sectional view of a cyst extractor.
Figure 4:
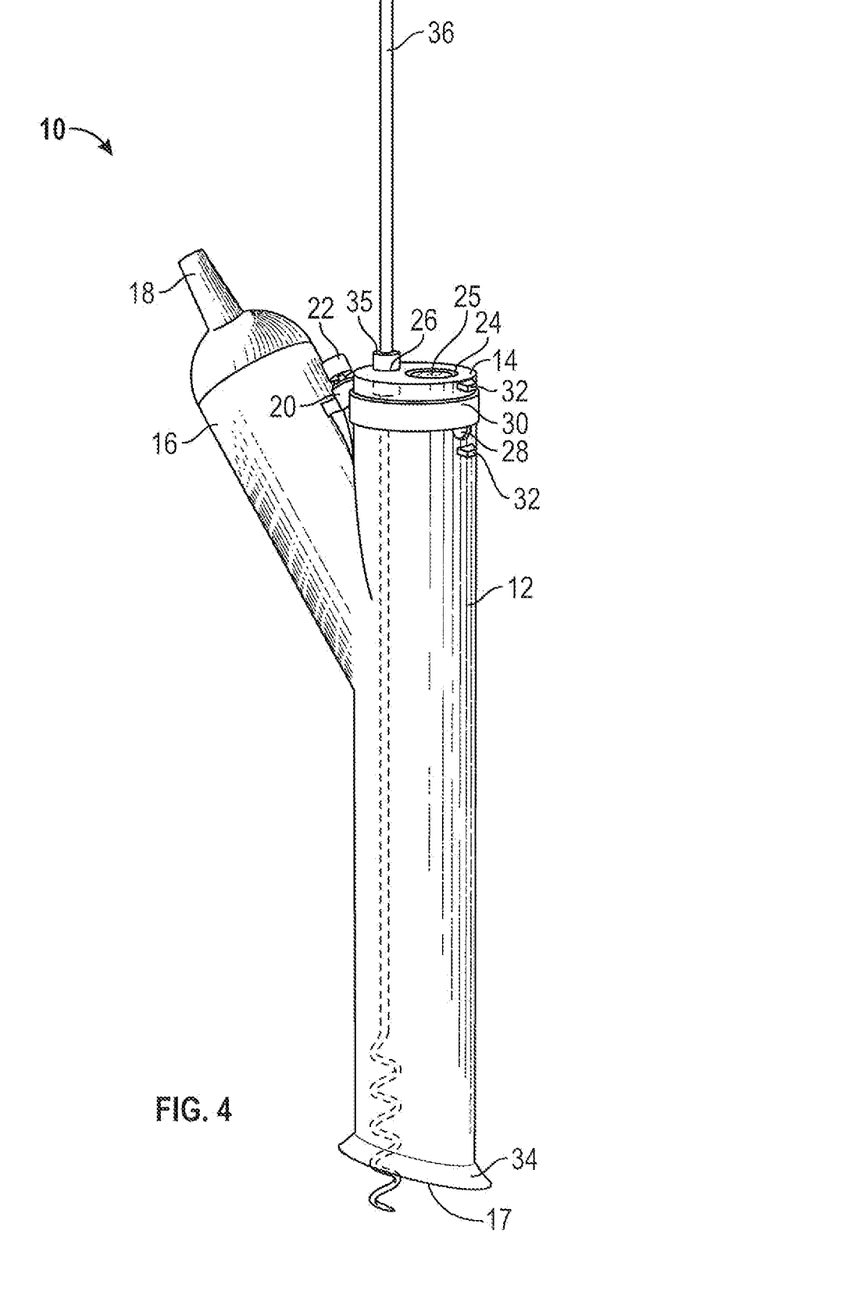
FIG. 4 is an isometric view of a cyst extractor with an auger needle.

The needle port 26 contains a seal 35 as shown in FIG. 4. The seal 35 is a pliable piece of material which fits within the needle port 26 and which has a smaller opening in its center. The seal 35 presses up around a needle inserted through the opening in its center. The seal 35 allows the needle to be moved around, while still keeping fluids from leaking out the needle port 26. The seal 35 may be formed from any material which is resilient or elastic enough to press around the needle and still allow the needle to move. The seal 35 may be formed from rubber, silicone, plastic or the like.

A needle 36 may be placed through the small opening in the center of the seal 35 and into the interior of the cyst extractor 10. The needle 36 should be longer than the tubular member 12 and the cap 14 together. The needle 36 is used to puncture the cyst or lesion such as a gallbladder or other puncturable cyst. The needle 36 can be a straight needle or else as illustrated in FIG. 4, the needle 36 may be an auger style or corkscrew needle. The auger needle 36 aids in the removal of semi-solid material from a cyst. The auger needle 36 dislodges any semi-solid or viscous material and hooks onto it, allowing the medical practitioner to pull the solid or semi-solid material from the cyst. The auger needle 36 may also aid in retracting the cyst into the cyst extractor 10.

The end of the tubular member 12 opposite the cap 14 is open 17 in order to allow it to be placed up against a lesion, such as a cystic tumor, abscess, gallbladder, or appendix.

The open end of the tubular member 12 is slanted slightly in order to make the cyst extractor 10 easier to insert into an incision in the patient's body and have the end of the tubular member 12 abut the surface of the lesion. When it is inserted into an incision in the patient's body, the open end 17 of the tubular member 12 is placed so that the entire opening is covered by the tissue forming the lesion.

The open end 17 of the tubular member 12 has a lip 34 that surrounds the open end 17 and which aids in sealing the cyst extractor 10 to the surface of the cyst in order to prevent leakage of the cyst's contents. The lip 34, as illustrated, surrounds the entire open end 17 of the tubular member 12 and is a ring of material coupled to the open end 17 of the tubular member 12 which increases the thickness of the tubular member's 12 material at that point. The lip 34 may be anything that aids in sealing the cyst extractor 10 to the surface of the cyst and which helps to prevent leakage of the contents of the cyst.

As shown in FIGS. 1-6, a trap 16 is coupled to the tubular member 12 and is in fluid communication with the tubular member 12. The trap 16 acts to catch any tissue, viscous, solid or semisolid material which is removed from the cyst. The trap 16 also holds that material in a location in the cyst extractor 10 where it will not impede the medical practitioner's view of the procedure. The trap 16 is an open chamber which branches off at an angle from the main tubular member 12. The trap 16 may be any size or shape desired so long as the trap 16 is large enough to hold all or most of the material removed from the cyst. The trap 16 may be translucent or transparent like the tubular member 12.

The trap 16 is in fluid communication with the tubular member 12 on one end and is in communication with a suction post 18 at the other end. The suction post 18 is a smaller tubular member that narrows towards the top. The suction post 18 is designed to have a medical suction machine coupled to its top end, which may also be the narrowest end. The bottom of the suction post 18 being coupled to the trap 16. The suction post 18 may, however, be formed in any shape desired so long as it allows a medical suction machine to be connected to the trap 16.

The suction post 18 may be in fluid communication with the trap 16 or may be limited to vacuum communication with the trap 16. If the suction post 18 is only in vacuum communication with the trap 16, a barrier may be placed between suction post 18 and the trap 16 which would allow suction to pass to the trap 16, but would prevent any material from traveling from the trap 16 into the suction post 18.

The suction machine applies suction to the entire cyst extractor 10. The suction pulls the material removed from the cyst into the trap 16. The suction also provides enough of a vacuum to pull the surface membrane of the cyst, abscess, gallbladder or an infected appendix into the cyst extractor 10. The suction machine may also provide enough suction to retract an organ into the open end 17 of the cyst extractor 10.

Suction may also be applied to the suction post 18 by a suction bulb or any other device or method which produces the desired amount of suction through the cyst extractor 10.

Figure 5:
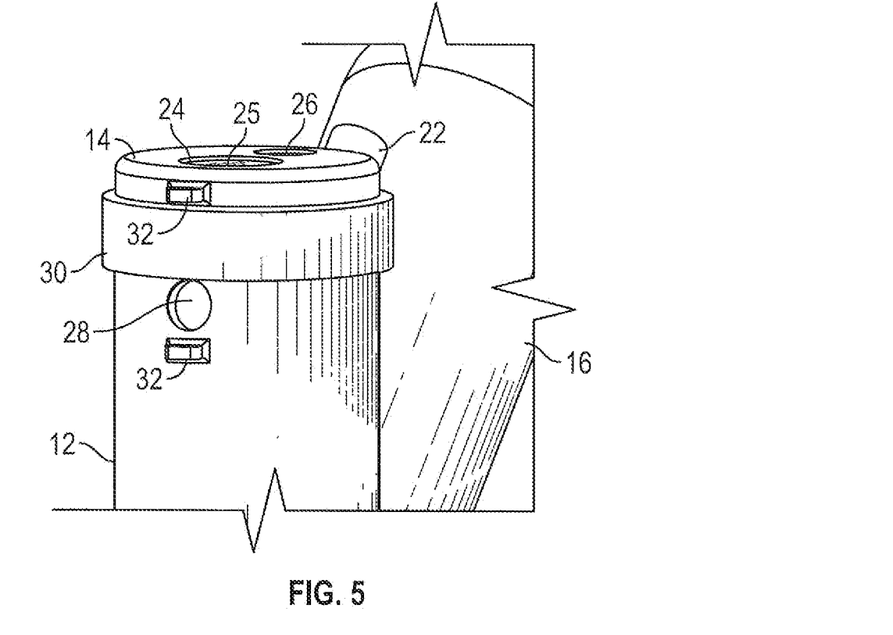
FIG. 5 is a view of an open vacuum break on a cyst extractor.
Figure 6:
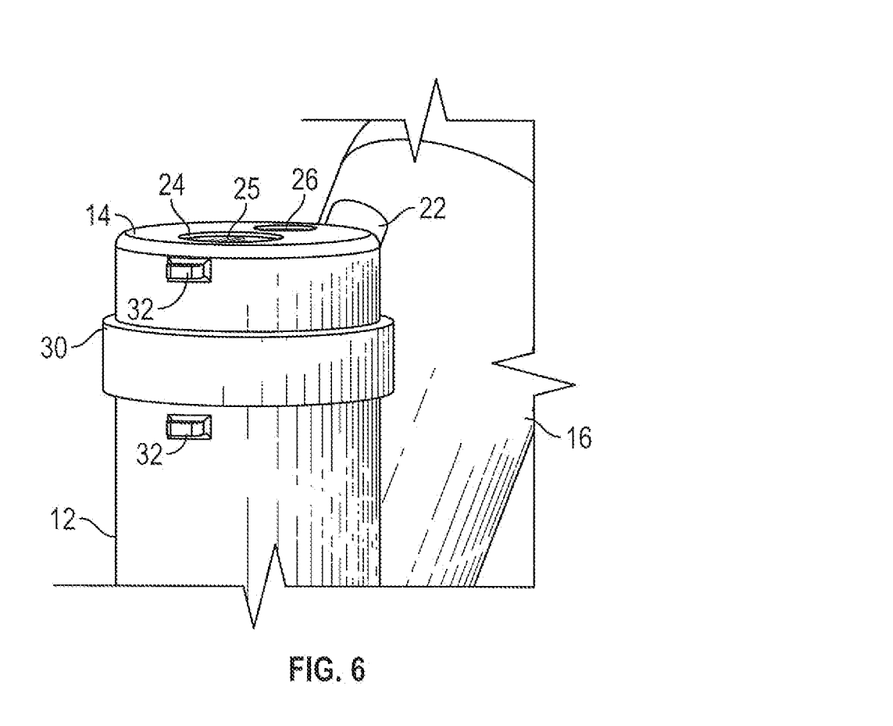
FIG. 6 is a view of a closed vacuum break on a cyst extractor.

The force of the suction within the cyst extractor 10 may be regulated by a vacuum break 28, illustrated in FIGS. 5 and 6. The vacuum break 28 is an opening in the cyst extractor 10. In the FIGs, the vacuum break 28 is illustrated as a round hole in the tubular member 12 of the cyst extractor 10. The vacuum break 28, however, may be any shape opening desired and may be located anywhere on the cyst extractor 10 that has suction applied.

The vacuum break 28 can be covered by vacuum break cover 30. Vacuum break cover 30 is a ring that surrounds the circumference of the tubular member 12 and slideably engages the tubular member 12 and moves between a raised position opening the entire vacuum break 28 and a lowered position completely covering the vacuum break. Vacuum break cover 30 is wide enough to completely cover the vacuum break 28 in the lowered position. The vacuum break cover 30 is used to adjust the vacuum break 28. If the vacuum break 28 is completely uncovered then the suction is low within the cyst extractor 10. If the vacuum break 28 is completely covered then the suction is as high as possible within the cyst extractor 10. If the vacuum break 28 is partially uncovered then the amount of suction within the cyst extractor 10 is between the amount within the cyst extractor 10 when the vacuum break 28 is completely open and when the vacuum break 28 is completely closed or covered.

The vacuum break cover 30, though illustrated as a ring can be in any shape or form that can be used to cover the vacuum break 28. For example, the vacuum break cover 30 could be the thumb of the medical practitioner. The medical practitioner's thumb could be placed partially or completely over the vacuum break 28 in order to cover it. The vacuum break cover 30 could also be a plate that slides in a channel. The vacuum break 28 would be located within the channel and the vacuum break cover 30 would slide in the channel in order to cover the vacuum break 28.

At least one cover stop 32 prevents the vacuum break cover 30 from sliding off of the cyst extractor 10. The at least one cover stop 32 will typically be two cover stops 32, one above the vacuum break cover 30 and one below the vacuum break cover 30.

The at least one cover stop 32 as illustrated in the FIGs are raised areas on the outer surface of the tubular member 12 of the cyst extractor 10. These raised areas are small slightly rectangular areas in the FIGs, however, they may be any type of raised area which would prevent the vacuum break cover 30 from sliding off of the cyst extractor 10. At least one cover stop 32 may be a circular raised area, a rectangular raised area, a square raised area, a pyramidal raised area or the like. At least one cover stop 32 may be formed directly into the cyst extractor 10 or 32 may be coupled to the cyst extractor 10.

A light post 20 is also coupled to the tubular member 12. The light post 20 is a solid translucent cylindrical member that extends from the tubular member 12 between the trap 16 and the main tubular member. The light post 20 is simply a solid translucent member which holds a light source 22. The light post 20 may be any size or shape desired so long as it is able to couple to or hold the light source 22 and allows the light to transmit through the entire cyst extractor 10. The light post 20 may be transparent or translucent.

The light source 22 may be standard surgical lighting i.e. fiberoptic cable or the light source 22 may be any light cable, light bulb or light source which is compact enough to couple to the light post 20 and which provides enough light for the procedure.

Figure 7:
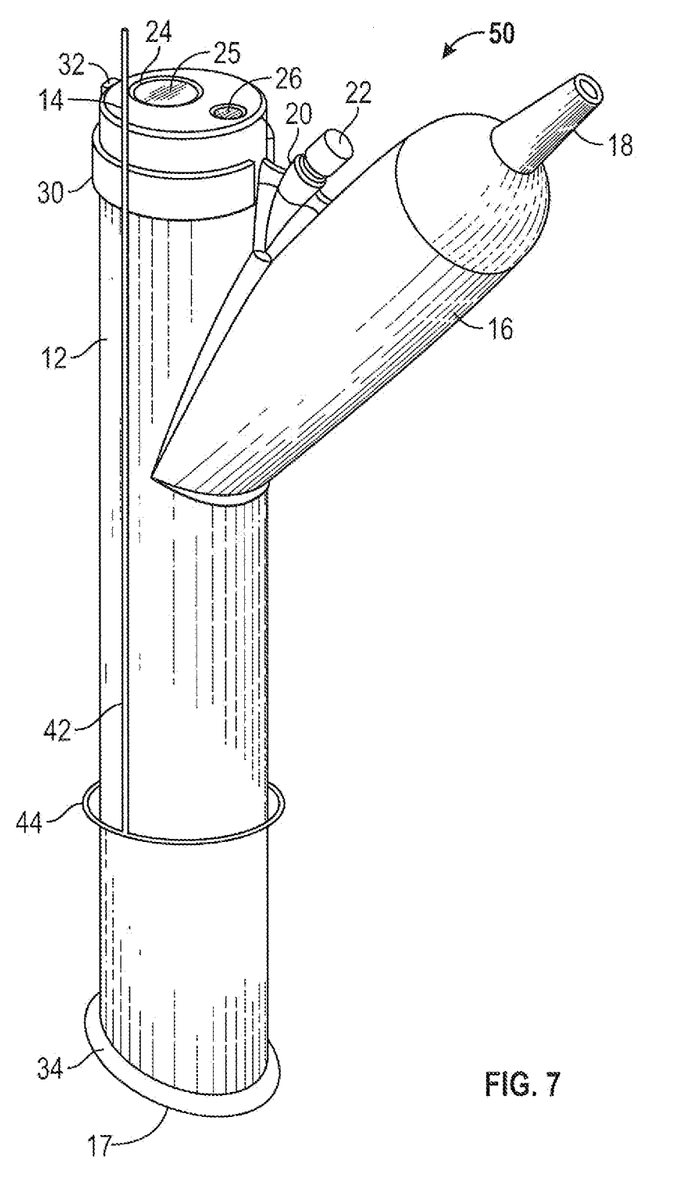
FIG. 7 is a view of a cyst extractor with a cutting wire.
Figure 8:
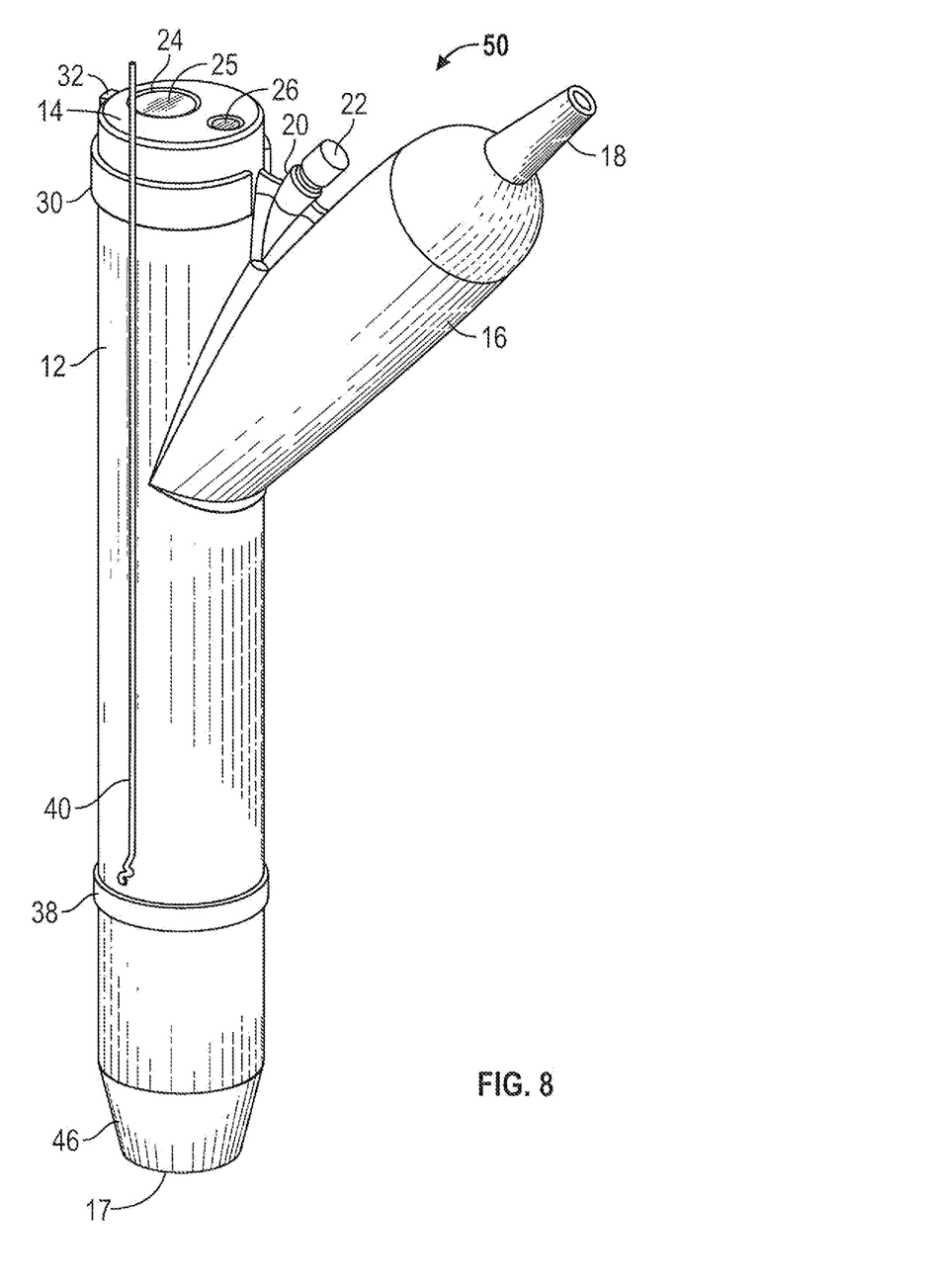
FIG. 8 is a view of a cyst extractor with a ligature deployer.
Figure 9:
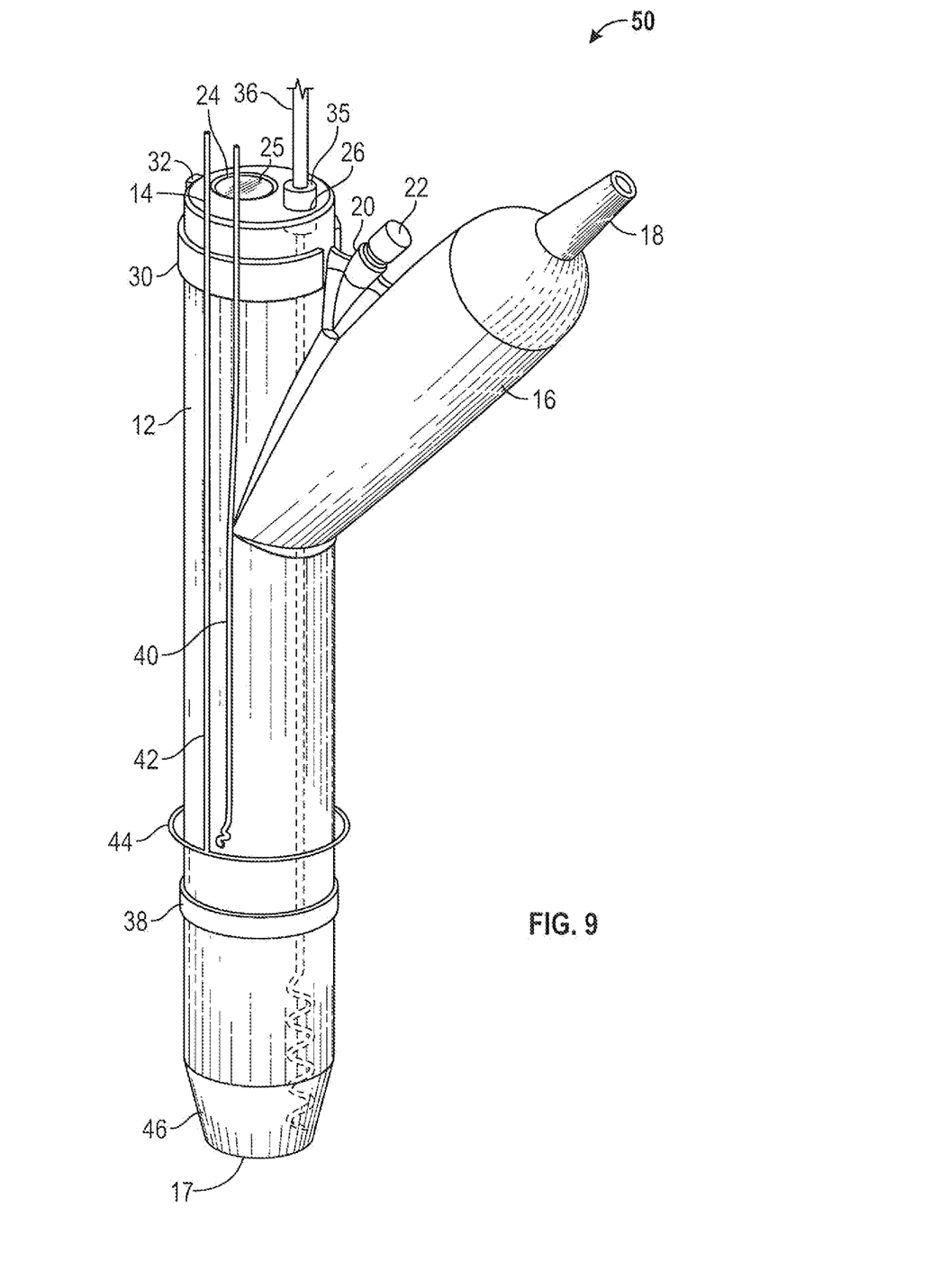
FIG. 9 is a view of a cyst extractor with both a cutting wire and a ligature deployer.

Variations of the cyst extractor 10 are illustrated in FIGS. 7-9. These variations are referenced as cyst extractor 50 and are for use on organs such as an appendix or gallbladder rather than for use on a pelvic cyst. These cyst extractors 50 include additional features in order to aid in the amputation of these specific cysts. Other than the variations discussed below, the cyst extractors 50 are identical to the cyst extractor 10 discussed above.

FIG. 7 illustrates a cyst extractor 50 that includes a cutting wire 44 and a wire handle 42. The cutting wire 44 is a ring of very thin wire that slices through tissue. The cutting wire 44 surrounds the tubular member 12 of the cyst extractor 50. The cutting wire 44 may also be an electrode in order to aid in cutting tissue.

The cutting wire 44 may be configured in a ring as illustrated in the FIGs or else it may be a small loop, arch or the like. The cutting wire 44 may be any shape desired provided it is able to amputate the cyst from its stump, vascular base or base.

The cutting wire 44 is coupled to the wire handle 42. The wire handle 42 allows the medical practitioner to manipulate the cutting wire 44 from the end of the cyst extractor 50 which is farthest from the cyst. The wire handle 42 may be any length, shape or material desired in order to serve its purpose. The wire handle 42 may be coupled to the cyst extractor 50 or it may be independent of the extractor 50.

FIG. 8 illustrates a cyst extractor 50 which includes a constricting ligature 38 and a ligature deployer 40. The constricting ligature 38 is an elastomeric ring similar to a hemorrhoidal constricting band that is used to constrict the blood in tissue. Constricting ligatures 38 such as this are used to stop blood flow between an organ such as the appendix and the base to which it is attached. Once the constricting ligature 38 has been placed around the base, the base can be severed without significant blood loss.

The constricting ligature 38 is positioned around the tubular member 12 of the cyst extractor 50. In this embodiment of the cyst extractor 50, the open end 17 of the tubular member 12 is tapered 46. The taper 46 is a narrowing of the diameter of the tubular member 12. This taper 46 allows the constricting ligature 38 to be slid off of the tubular member 12 and around the base and vascular supply of the lesion.

The constricting ligature 38 is pushed off of the tubular member 12 and down the taper 46 by a ligature deployer 40. The ligature deployer 40 may be a wire with a handle which pushes the constricting ligature 38 forward. The ligature deployer 40 may be any device that serves the purpose of allowing the medical practitioner to push the constricting ligature 38 onto the base of the lesion from the end of the cyst extractor 50 which will be closest to the medical practitioner during the procedure. The ligature deployer 40 may be coupled to the cyst extractor 50 or it may be independent of the extractor 50.

FIG. 9 illustrates an embodiment of the cyst extractor 50 which includes both a cutting wire 44 and a constricting ligature 38. Often in a surgery it will be desirable to place a constricting ligature 38 on a base of a cyst and then amputate the lesion from the vascular base with a cutting wire 44. Therefore, it may be desirable to have both of these features on a cyst extractor 50.

In alternate embodiments of the cyst extractor 50, the needle port 26 may be removed. Some cysts are small enough that they do not need to be punctured and the contents aspirated prior to the diseased lesion being retracted into the cyst extractor 50.

In additional embodiments, the cyst extractor might function as the specimen container for processing, and obviating handling of infected or contaminating fluids and tissues by medical practitioners. In this embodiment, additional lids might be used to close off the various openings in the cyst extractor in order to prevent leaking or spilling of the fluids and tissues.

Accordingly, for the exemplary purposes of this disclosure, the components defining any embodiment of the invention may be formed as one piece if it is possible for the components to still serve their function. The components may also be composed of any of many different types of materials or combinations thereof that can readily be formed into shaped objects provided that the components selected are consistent with the intended mechanical operation of the invention. For example, the components may be formed of rubbers (synthetic and/or natural), glasses, composites such as fiberglass, carbon-fiber and/or other like materials, polymers such as plastic, polycarbonate, PVC plastic, ABS plastic, polystyrene, polypropylene, acrylic, nylon, phenolic, any combination thereof, and/or other like materials, metals, such as zinc, magnesium, titanium, copper, iron, steel, stainless steel, any combination thereof, and/or other like materials, alloys, such as aluminum, and/or other like materials, any other suitable material, and/or any combination thereof.

Figure 10:
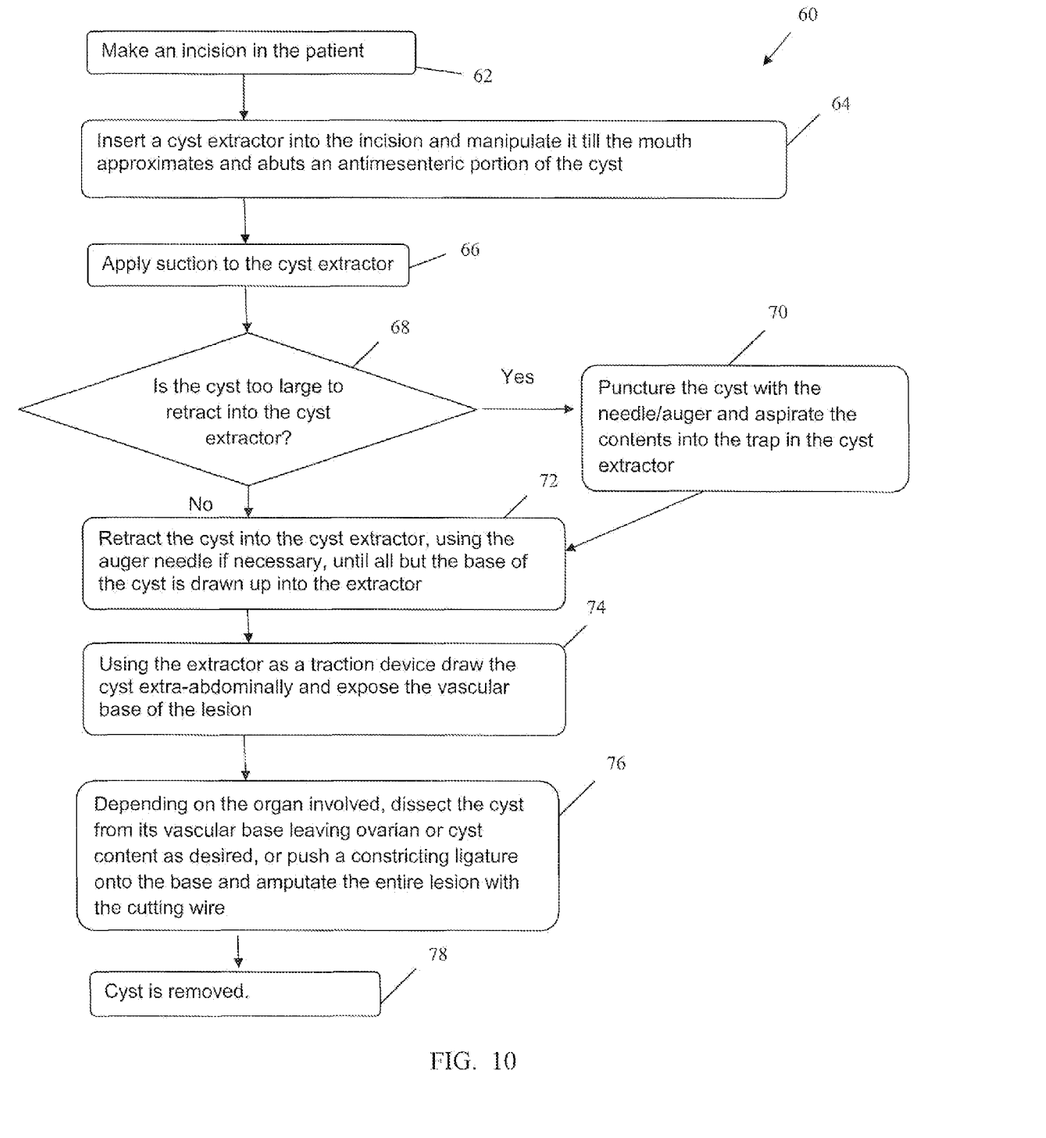
FIG. 10 is a flow chart of a method of using a cyst extractor.

A method of using a cyst extractor 60 as depicted in FIG. 10 includes first, making an incision in the patient 62. The incision should be near the location of the cyst to be removed. The cyst may be a cyst, abscess, appendix, gallbladder or the like.

Next, the medical practitioner inserts a cyst extractor into the incision 64. The medical practitioner manipulates the cyst extractor so that the open end 17 of the tubular member of the cyst extractor approximates and abuts an antimesenteric portion of the cyst.

The cyst extractor may be configured to include a cutting wire and/or constricting ligature depending on the nature of the lesion which is being removed. If the lesion is a cyst, such as an ovarian cyst, the cyst extractor will not include a cutting wire or a constricting ligature. The cyst extractor will, however, include the needle port so that the contents of the cyst can be drained and augered.

If the lesion to be removed is an appendix, then the cyst extractor will not include a needle port. The cyst extractor will, however, include a cutting wire and a constricting ligature.

If the lesion to be removed is a gallbladder, then the cyst extractor will include a needle port, cutting wire and a constricting ligature.

Next, suction is applied to the cyst extractor 66 by attaching a medical suction machine to the suction post. The amount or strength of the suction may be controlled by opening or closing the vacuum break partially or completely.

Now the medical practitioner must determine if the lesion is small enough to be retracted fully into the cyst extractor 68. If the lesion is an appendix or even a small cyst, then the medical practitioner may decide to retract the entire cyst into the cyst extractor 72. If the medical practitioner decides to retract the entire cyst into the cyst extractor, the medical practitioner may insert the auger needle into the needle port. The medical practitioner may then use the auger needle to hook and draw the cyst into the cyst extractor. The cyst is retracted into the cyst extractor until only the base of the cyst remains outside the cyst extractor.

The cyst may also be retracted into the cyst extractor using only suction and not the auger needle.

If the lesion is not small enough to be retracted fully into the cyst extractor 68, i.e. the diseased part or lesion is a large ovarian cyst or gallbladder, then the medical practitioner will insert a needle into the needle port. The needle will be used to puncture the lesion in order to aspirate the contents of the lesion and collapse it into the trap in the cyst extractor 70. A straight needle may be used for this step in the method, if the lesion is filled with a simple fluid. If, however, the lesion is filled with semi-solid or solid material, i.e. it is a gallbladder full of gallstones or grit, a sebaceous cyst or a dermoid cyst, etc., then an auger needle is used in order to aid the movement of the solid or semi-solid material into the cyst extractor.

Once the contents of the lesion have been aspirated, the lesion can be retracted into the cyst extractor 72. Often the lesion will be retracted into the cyst extractor until only the base remains outside the cyst extractor 72. The auger needle may be used to aid in retracting the lesion into the cyst extractor.

When the lesion is partially or fully retracted into the cyst extractor, the medical practitioner can repair anything that needs to be repaired. For example, if the lesion was an ovarian cyst, the medical practitioner may retract the ovary into the cyst extractor and may perform surgery on the ovary under the mild retractive force of the suction in the extractor. The ovary can then be returned to the patient's body.

Using the cyst extractor as a traction device, the medical practitioner can also draw the cyst extra-abdominally in order to expose the vascular base of the lesion 74. In some cases it may not be necessary to draw the cyst entirely out of the body in order to access the base of the cyst.

Depending on the organ involved, the medical practitioner can then dissect the cyst from its vascular base leaving ovarian or cyst content as desired 76. If the cyst is an appendix, a gallbladder or the like, the medical practitioner may now push the constricting ligature onto the vascular base in order to limit or stop the blood flow to the cyst 76. Once the constricting ligature has been pushed onto the stump, the cutting wire may be used in order to sever the stump and amputate the cyst 76.

Once the cyst or lesion is no longer attached it may be removed 78. The embodiments and examples set forth herein were presented in order to best explain the present invention and its practical applications and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims. Accordingly, any components of the present invention indicated in the drawings or herein are given as an example of possible components and not as a limitation.

The invention claimed is:

1. A cyst extractor comprising:
    a tubular member, wherein said tubular member is translucent;
    a cap coupled to an end of said tubular member, wherein said cap further comprises at least one view port and at least one needle port;
    a trap in fluid communication with said tubular member, wherein the trap bifurcates at an acute angle from the tubular member and wherein the diameter of the tubular member is substantially equal to the diameter of the trap;
    a suction post in communication with said trap; and
    a light post coupled to said tubular member between the trap and the cap coupled to an end of said tubular member.

2. The cyst extractor of claim 1, further comprising a vacuum break in fluid communication with said suction post.

3. The cyst extractor of claim 1, further comprising an auger needle inserted through said needle port.

4. The cyst extractor of claim 1, wherein said at least one view port further comprises a magnifying lens.

5. The cyst extractor of claim 1, further comprising suction applied to said suction post.

6. The cyst extractor of claim 1, further comprising an amputating wire coupled to said tubular member.

7. The cyst extractor of claim 1, wherein the entire tubular member is translucent.

8. A cyst extractor comprising:
a transparent tubular member;
a cap coupled to one end of said transparent tubular member, wherein said cap further comprises at least one view port;
a trap in fluid communication with said transparent tubular member, wherein the trap bifurcates at an acute angle from the tubular member and wherein the diameter of the tubular member is substantially equal to the diameter of the trap;
a suction post in communication with said trap;
a light post coupled to said transparent tubular member between the trap and the cap coupled to one end of said transparent tubular member;
a ligature deployer coupled to said transparent tubular member; and
a cutting wire coupled to said transparent tubular member.

9. The cyst extractor of claim 8, wherein said cap further comprises at least one needle port.

10. The cyst extractor of claim 9, further comprising a needle inserted through said at least one needle port.

11. The cyst extractor of claim 10, wherein said needle is an auger needle.

12. The cyst extractor of claim 8, further comprising a light source coupled to said light post.

13. The cyst extractor of claim 8, further comprising an adjustable vacuum break in fluid communication with said suction post.

14. The cyst extractor of claim 8, wherein the entire tubular member is transparent.

\* \* \* \* \*